United States Patent
Sussman et al.

(10) Patent No.: US 7,303,872 B2
(45) Date of Patent: *Dec. 4, 2007

(54) METHOD OF ERROR REDUCTION IN NUCLEIC ACID POPULATIONS

(75) Inventors: Michael R. Sussman, Madison, WI (US); Francesco Cerrina, Madison, WI (US); Peter J. Belshaw, Madison, WI (US); James H. Kaysen, Madison, WI (US); Kathryn Richmond, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/376,720

(22) Filed: Feb. 28, 2003

(65) Prior Publication Data

US 2004/0132029 A1 Jul. 8, 2004

Related U.S. Application Data

(60) Provisional application No. 60/360,563, filed on Feb. 28, 2002.

(51) Int. Cl.
*C12Q 1/68* (2006.01)
*C07H 21/04* (2006.01)
*C12P 19/34* (2006.01)

(52) U.S. Cl. ............... 435/6; 435/91.2; 536/24.31; 536/24.32

(58) Field of Classification Search ............... 435/6, 435/91.2; 536/23.1, 24.31, 24.32
See application file for complete search history.

(56) References Cited

U.S. PATENT DOCUMENTS

| | | | |
|---|---|---|---|
| 5,376,526 A | 12/1994 | Brown et al. | |
| 6,027,877 A | 2/2000 | Wagner, Jr. | |
| 6,120,992 A | 9/2000 | Wagner, Jr. | |
| 6,287,825 B1 * | 9/2001 | Weissman et al. | 435/91.2 |
| 6,297,010 B1 | 10/2001 | Stefano | |
| 6,586,211 B1 | 7/2003 | Stahler et al. | |
| 6,670,127 B2 | 12/2003 | Evans | |
| 6,673,552 B2 * | 1/2004 | Frey | 435/6 |
| 7,183,406 B2 * | 2/2007 | Belshaw et al. | 536/25.3 |
| 2003/0068633 A1 * | 4/2003 | Belshaw et al. | 435/6 |
| 2003/0186226 A1 | 10/2003 | Brennan et al. | |
| 2005/0287585 A1 | 12/2005 | Oleinlkov | |

FOREIGN PATENT DOCUMENTS

EP 1 041 160 A1 10/2000
WO WO 9954498 A1 * 10/1999

OTHER PUBLICATIONS

Singh-Gasson et al. Maskless fabrication of light-directed oligonucleotide microarrays using a digital micromirror array. Nature Biotechnology, vol. 17, p. 974-978, 1999.*
Prodromou, C., et al., "Recursive PCR: a novel technique for total gene synthesis," Protein Engineering 5:827-829 (1992).
Soderlind, E., et al., "Domain libraries: Synthetic diversity for de novo design of antibody V-regions," Gene 160:269-272 (1995).
Stemmer, W. P.C., et al., "Single-step assembly of a gene and entire plasmid from large numbers of oligodeoxyribonucleotides," Gene 164:49-53 (1995).
Alani, E., et al., "The *Saccharomyces cerevisiae* Msh2 protein specifically binds to duplex oligonucleotides . . . ," Genes & Development 9:234-247 (1995).
Hughes, M.J., et al, "The Purification of a Human Mismatch-binding Protein and Identification . . . ," J. of Biological Chemistry 267:23876-23882 (1992).
Nelson, S.F., "Genomic mismatch scanning: Current progress and potential applications," Electrophoresis 16:279-285 (1995).

* cited by examiner

*Primary Examiner*—Suryaprabha Chunduru
(74) *Attorney, Agent, or Firm*—Quarles & Brady LLP

(57) ABSTRACT

A method is disclosed for the direct synthesis of double stranded DNA molecules of a variety of sizes and with any desired sequence. The DNA molecule to be synthesis is logically broken up into smaller overlapping DNA segments. A maskless microarray synthesizer is used to make a DNA microarray on a substrate in which each element or feature of the array is populated by DNA of a one of the overlapping DNA segments. The complement of each segment is also made in the microarray. The DNA segments are released from the substrate and held under conditions favoring hybridization of DNA, under which conditions the segments will hybridize to form duplexes. The duplexes are then separated using a DNA binding agent which binds to improperly formed DNA helixes to remove errors from the set of DNA molecules. The segments can then be hybridized to each other to assemble the larger target DNA sequence.

7 Claims, 5 Drawing Sheets

SEQUENCE LISTING

<160> NUMBER OF SEQ ID NOS: 4

<210> SEQ ID NO 1
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 1
gttaatgggc acaaattttc tgtcagtgga gagggtgaag       40

<210> SEQ ID NO 2
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 2
cttcaccctc tccactgaca gaaaatttgt gcccattaac       40

<210> SEQ ID NO 3
<211> LENGTH: 39
<212> TYPE: DNA
<213> ORGANISM: Artificial

-continued

```
<220> FEATURE:
<223> OTHER INFORMATION: Synthetic Oligonucleotide

<400> SEQUENCE: 3
cttcaccctc tccactgacg aaaatttgtg cccattaac                              39

<210> SEQ ID NO 4
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 4
cttcaccctc tccactgaaa gaaaatttgt gcccattaac                             40
```

METHOD OF ERROR REDUCTION IN NUCLEIC ACID POPULATIONS

CROSS REFERENCE TO RELATED APPLICATION

This application claims the benefit of U.S. Provisional Application No. 60/360,563 filed Feb. 28, 2002.

STATEMENT REGARDING FEDERALLY SPONSORED RESEARCH OR DEVELOPMENT

This invention was made with United States government support awarded by the following agency: DOD ARPA Grant #: N39998-01-2-7070. The United States has certain rights in this invention.

BACKGROUND OF THE INVENTION

This invention pertains generally to the field of biology and particularly to techniques and apparatus for the manufacture of DNA molecules of defined or desired sequences. The manufacture of DNA molecules also makes possible the synthesis of any desired peptides, proteins or assemblies of proteins and nucleic acids as may be desired.

Using the techniques of recombinant DNA chemistry, it is now common for DNA sequences to be replicated and amplified from nature and for those sequences to then be disassembled into component parts which are then recombined or reassembled into new DNA sequences. While it is now both possible and common for short DNA sequences, referred to a oligonucleotides, to be directly synthesized from individual nucleosides, it has been thought to be generally impractical to directly construct large segments or assemblies of DNA sequences larger than about 400 base pairs. As a consequence, larger segments of DNA are generally constructed from component parts and segments which can be purchased, cloned or synthesized individually and then assembled into the DNA molecule desired.

For example, if an expression vector is desired to express a new protein in a selected host, the scientist can often purchase a generic expression vector from a molecular biology supply company and then clone or synthesize the protein coding region for the gene sought to be expressed. The coding region must be ligated into the vector in such a manner and in the correct location and orientation such that the vector will be effective to express the desired protein in the host. The purchaser of the vector must also examine the sequence of the vector to make sure no other DNA component of the vector has other properties that might be detrimental to the experiment the purchaser wishes to run. Thus, the difficulty in constructing any new desired larger DNA construct is dependent on what similar constructs, or what components of the construct, can be purchased or obtained from public sources, and how much information is available about the sequences of those components.

A novel methodology to construct and assemble newly designed DNA sequences of indefinite length has been developed based on the use of DNA constructed in DNA microarrays. A DNA microarray is made up of a plurality of sets of single stranded DNA probes arranged on a substrate. The sets of probes are identical in nucleotide sequence but different in sequence from other sets of probes. A technique has been described for the in situ synthesis of DNA microarrays that is adapted for the manufacturing of customized arrays. Published PCT patent application WO99/42813 and U.S. Pat. No. 6,375,903 describe a method for making such arrays in which the light is selectively directed to the array being synthesized by a high density micromirror array under software control from a computer. Since the micromirror array is operated totally under software control, the making of complex and expensive photolithographic masks is avoided in its entirety. It has been previously proposed that such custom microarrays can be used to provide the single stranded DNA segments necessary and sufficient to assemble double stranded DNA molecules of indeterminate length. In PCT published patent application WO 02/095073, the disclosure of which is hereby incorporated by reference, this process is set forth. In short, using that approach, short segments of single stranded DNA are made on the microarray and designed such that a portion of each probe is complementary to two other oligonucleotides in another set on the array. In theory then, when the oligonucleotides are released from the substrate of the array, the DNA segments will self-assemble into the complete desired DNA molecule as each complementary segment hybridizes to its complement.

A complexity arises from this general approach to DNA synthesis that no synthetic or biochemical processes are ever completely efficient and accurate. Thus it is inevitable that there will be occasional deletion and substitution errors in the DNA segments made by this process. To facilitate the practical synthesis of longer DNA molecules on interest and of good quality, methods must be developed to purify the DNA sequences of interest from those artifacts that arise through various sorts of errors and inefficiencies in the probe synthesis and assembly process.

BRIEF SUMMARY OF THE INVENTION

The present invention is summarized in a method for separation of DNA molecules of correct sequence away from DNA molecule of incorrect sequence, the method including the steps of exposing a solution of double stranded DNA molecules to a DNA binding agent which will binds selectively to duplex DNA molecules having a topographical irregularity; and separating the DNA molecules to which the DNA binding agent bound from those DNA molecules to which the DNA binding agent did not bind.

This invention makes practical the construction to order of DNA constructs of virtually any size with minimal error. This frees the experimenter who wishes to perform experiments on DNA or on gene expression from the constraints of working with commercially available vectors or genetic elements. Instead, DNA sequences can be invented on a computer and fabricated for the first time and in a short time period using this microarray based technique.

The present invention is also directed to a method for separating out DNA duplexes carrying a minority sequence from a pool of such sequences carrying a majority sequence. This method includes the steps of denaturing the duplex DNA molecules; permitting the DNA molecules to hybridize to form new DNA duplex molecules; exposing the duplex DNA molecules to a DNA binding agent that binds selectively to DNA molecules having an irregularity in the topology of the DNA duplex; and separating the DNA molecules by separation out of those DNA molecules to which the DNA binding agent bound.

Further objects, features and advantages of the invention will be apparent from the following detailed description when taken in conjunction with the accompanying drawings.

DETAILED DESCRIPTION OF THE INVENTION

Figure 1:
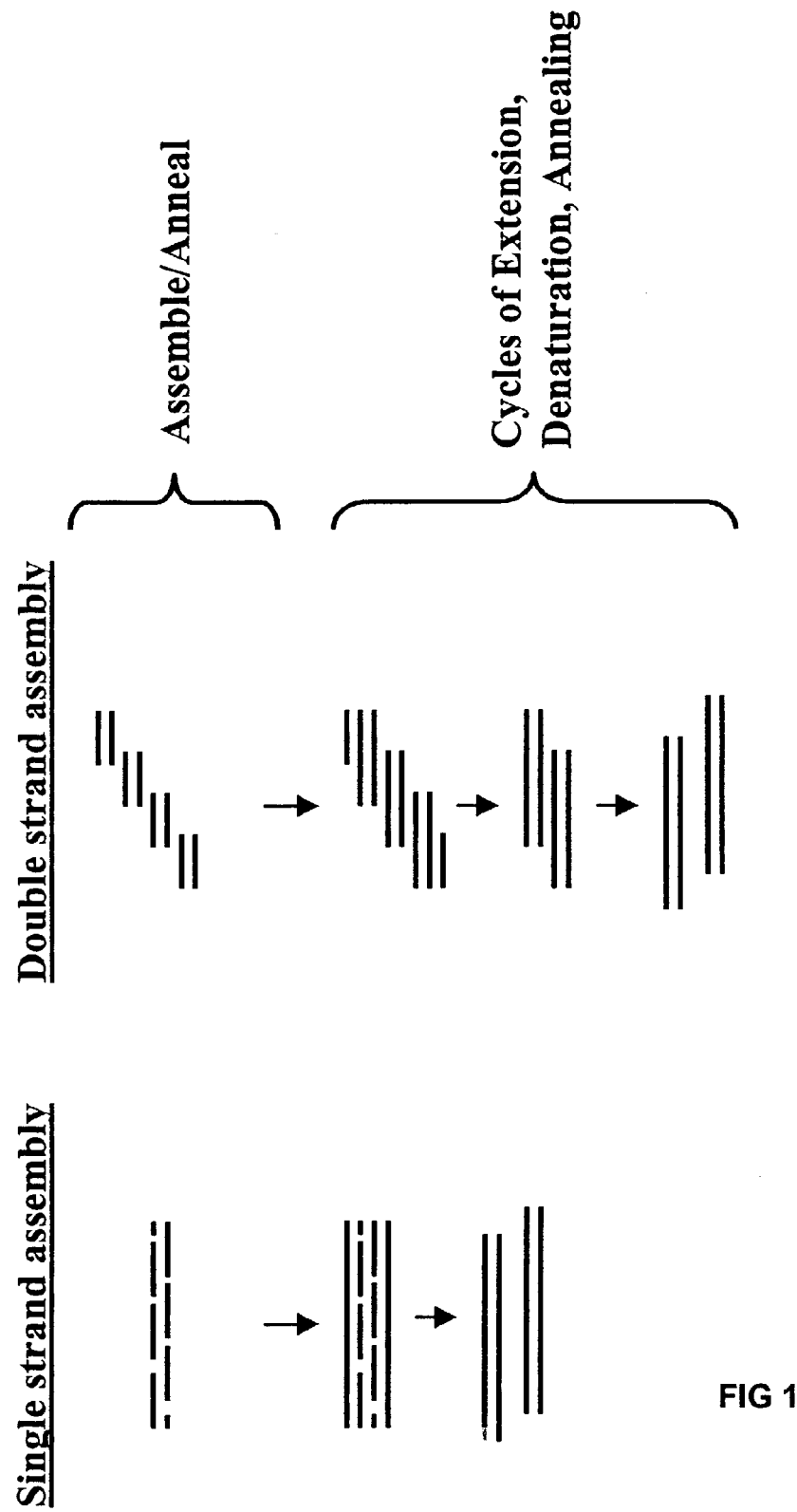
FIG. 1 illustrates schematically the approach of the present invention.

In one embodiment, the present invention originated as a method for reducing the amount of error produced during the synthesis of double stranded oligonucleotides. We refer to this method as "coincidence filtering." The term "coincidence filter" is borrowed from electronics and optical physics, where a coincidence filter is used to filter for light or energy signals that are coincident. Here the is used to refer to a process which selectively permits to pass through the process only those DNA segments with are coincident, or which have no unpaired or mis-paired nucleotides. This process removes from the nucleic acid populations those nucleic acids that have mismatches or deletions internally within them. The overall process also includes a method to selectively filter out any double stranded DNA molecules which have a correct, matched sequence but have a sequence that is different from the sequence of the majority of DNA sequences in the population of DNA molecules made.

The method of the present invention arose out of efforts to make a general purpose DNA synthesis process using the massively parallel DNA fabrication capabilities of the maskless DNA synthesis instrument, of the type described in U.S. Pat. No. 6,375,903, the disclosure of which is also incorporated herein by reference. The maskless array synthesizer permits many single stranded DNA probes to be fabricated in parallel in a short time, under computer control. This technology permits the manufacture in a few hours of a custom DNA microarray in which the single stranded DNA probes in the array can be of any arbitrary DNA sequence. The microarray is arranged in features where all the probes in a given feature are of the same DNA sequence, which can differ from the sequence of the probes in any other feature. This technology permits the synthesis of tens to hundreds of thousands of different features in a single microarray, each feature composed of DNA probes of 20 to 150 nucleotides in length, in a matter of hours. Here, the microarray synthesis instrument is used as a massively parallel generator of single stranded DNA segments, and the process described here is concerned with assembling those segments into a long piece of DNA while eliminating errors in the synthesis process.

The technology described in the previously mentioned PCT published application WO 02/095073 already envisions the use of the massively parallel DNA synthesis capability of the maskless array synthesizer to be used to make very long DNA sequences of interest. The present invention is directed toward processes for solving, among other things, the following problem. Consider that every step in the addition of nucleotides to the DNA probes in the microarray is 99% efficient and accurate. That level of efficiency would mean that for every 100 nucleotides added, one nucleotide is either not added at all or is added in the wrong place. This rate of error would mean that if the DNA segments are all 25-mers, or composed of oligonucleotides 25 nucleotides in length, one out of every four probes, on average, would have an error in it. While the actual efficiency can, in reality, be made higher than 99%, the error rate cannot even be zero. Some number of the probes will have an error. The error can be any of the following: a failure to add a nucleotide, i.e. a deletion; an addition of a nucleotide in an incorrect location, i.e. an addition; a complete misplacement of one nucleotide for another, i.e. a substitution; or a chemical modification of a nucleotide. The purification process should therefore be arranged so as to remove from the population sequences made during the hybridization process as many as possible of the probes that contain an error, regardless of the type of error. The method described here will do that. It should be understood that while this process in designed and intended to solve this specific problem of DNA purification and separation in the context of using the microarray technique for DNA synthesis, this same process will be useful in any other DNA synthesis procedures in which it is desired to ultimately obtain copies of a single DNA molecule of interest.

Referring to FIG. 1, it was first thought, and described in the specification of WO 02/095073, that the assembly of the target DNA would be performed in a single step after the probes are released from the substrate of the microarray. That concept is illustrated in the left-hand illustration in FIG. 1. Using this basic approach, the DNA sequence of the probes in each feature overlaps partially the DNA sequence in the probes of two other features. Here, an addition to that strategy is contemplated. Here, it is suggested that on the microarray both the sense and antisense strand of every segment of DNA be constructed on the microarray. In other words, for each of the features on the array in, somewhere else on the array is a feature in which the probes have the exact complementary sequence. This might seem wasteful of DNA synthesis capacity, since this cuts the theoretical yield from a single microarray by one-half. However, since the capacity of this method of DNA synthesis is quite large, this waste is not significant, and the advantage of this strategy will become apparent in a moment.

Once the microarray with complementary sequence probes is made, the probes are released from the substrate. If one heats the solution of DNA strands thus made and then permits the solution to cool slowly, each probe will have the opportunity to find and hybridize to its exact complement. This is illustrated in the right-hand side of FIG. 1. Thus a large number of double stranded oligonucleotides are created, each equal in length to the length of the probes fabricated on the microarray. At this point, the double stranded DNA oligonucleotides do not self assemble into a larger DNA molecule but instead are simply short double stranded DNA segments.

This population of double stranded oligonucleotides will include some double stranded segments that have errors in them on one or the other of their single strand. Again, the most common errors will be of three kinds, a deletion, an addition or a substitution. If one assumes only that the errors are rare, each single strand that has an error in it will be most likely to hybridize to a complementary strand that does not have a perfectly complementary sequence. It will be exceedingly unlikely that for any probe fabricated with an error that the complementary strand for that probe will have been fabricated with an exactly complementary error. Thus for the double stranded DNA segments that were just created, the ones that have errors will have a mismatched nucleotide.

This mismatch in sequence, whether it is a deletion, addition or substitution, will cause a topographical irregularity in the double stranded DNA. In simple words, the double stranded DNA molecule will have a bump or bulge in it caused by an extra of a mismatched nucleotide. Notice in FIG. 5, intending to illustrate some of the DNA strands used in the examples below, that the deletion of a single nucleotide causes a topographical irregularity in the double stranded DNA, as the non-matching nucleotide is pushed out of the orderly double helix of the DNA. This same topographical irregularity occurs whether the error is a deletion, an insertion or a substitution. In each of these cases, the nucleotides in the two DNA strands do not align, as they should. As a first step, the process described here is intended to filter or separate out the double stranded DNA molecules that have a base pair mismatch from those that are perfectly matched. In that way, double stranded DNA segments having errors on either strand will be eliminated from the population.

Figure 2:
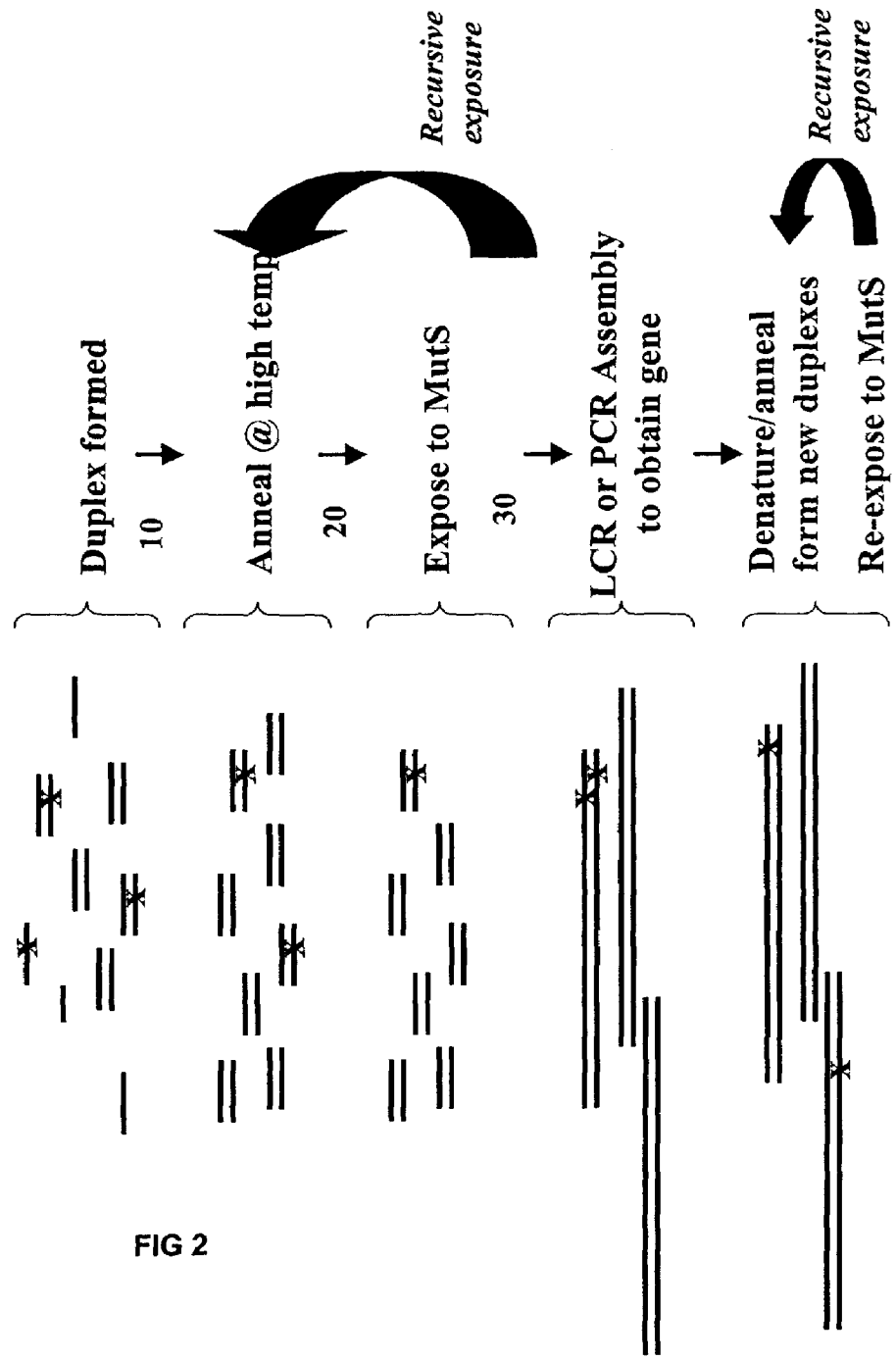
FIG. 2 illustrates schematically other steps in the approach of the present invention.

This process is illustrated schematically in FIG. 2. At the top of FIG. 2, in the step labeled 10, the single stranded DNA segments have been formed and released from the substrate on which they were made. The single stranded DNA has been formed into double stranded duplexes. The errors are indicated by the letter X. Where there is an error, that strand will hybridize to a strand that is complementary, but which does not have the same error. Then the duplexes formed are exposed to a DNA binding agent that selectively binds to DNA of improper helical shape. The preferred embodiment of such an agent is MutS, a bacterial protein associated with intracellular DNA correction mechanisms. MutS will preferentially bind to DNA that has an improper bump or loop in it caused by a strand mismatch. The DNA duplexes that have the binding agent adhered to them are then removed from the total population or pool of DNA duplexes. This is conveniently done by then doing a separation of the total pool of DNA duplexes using an affinity separation for the DNA binding agent. Referring to FIG. 2, the step labeled 20 refers to the step of annealing the single stranded probes into duplexes. The step labeled 30 refers to the step of applying the binding agent, such as MutS, and separating out the duplexes to which the binding agent binds. The step 30 may not be completely efficient in a single performance and it may be desirable to perform the steps 20 and 30 recursively as many times as appropriate to purify the duplexes to a desired degree of absence of error sequences.

It is still necessary at this point to assemble the short duplex DNA segments into the entire desired target DNA. This can be done a number of ways. Shown in FIG. 2 is the concept of using ligase chain reaction (LCR) or polymerase chain reaction (PCR) to complete defined sequences. Another approach is to heat the duplexes, to denature them, and then cool the solution more quickly than in the previous step of short duplex formation. The single DNA strands will again hybridize, but not all of them will re-hybridize with the short complementary probes. Remember that each single DNA strand has two DNA strands, other than its exact complement, to which it may hybridize. These other strands are the original DNA probes that were constructed to have a sequence which overlaps the complement of the first strand. So some of the single strands will now hybridize to the one-half complement strands. DNA polymerase can be used to fill out the partially double stranded/partially single stranded complexes thus made, and the step can be repeated again, as many times as necessary, until the large target DNA molecule is assembled.

Note that once the large DNA duplex molecules have been assembled, it is still possible to use the coincidence filter technique to remove erroneous sequences, assuming only that most of the sequences are correct. If one considers a pool of longer double stranded DNA molecules, most of which are correct in sequence and matching on both strands. To consider the worst case, let us assume that an error, which again could be a deletion, an insertion or a substitution, happened to occur on a part of a single strand which did not hybridize to a complement and then the single strand was extended using a DNA polymerase. The DNA polymerase will fill in the matching nucleotides based on the template on the single strand, and thus will fill in a complement to the error. The double stranded DNA will not at this point exhibit an improper DNA helix topology, since the two strands of that molecule are complementary. To filter out these errors, the process is to take all of these longer DNA strands, again heat them to denature them, and again cool them quickly. It is highly unlikely that the strand containing the error will again hybridize to the complementary strand having its same error. Instead, it is far more likely that the strand containing the error will mate to a correct complementary strand, not having the error, thus introducing a conformation irregularity in the duplex formed at the point of the error. The same thing will happen to the complementary strand. Then it is again possible to expose the duplexes to the binding agent, such as MutS, and remove from the pool those duplex molecules to which the MutS will bind. Again this step can be repeatedly recursively until a desired level of statistical purity is achieved.

Figure 3:
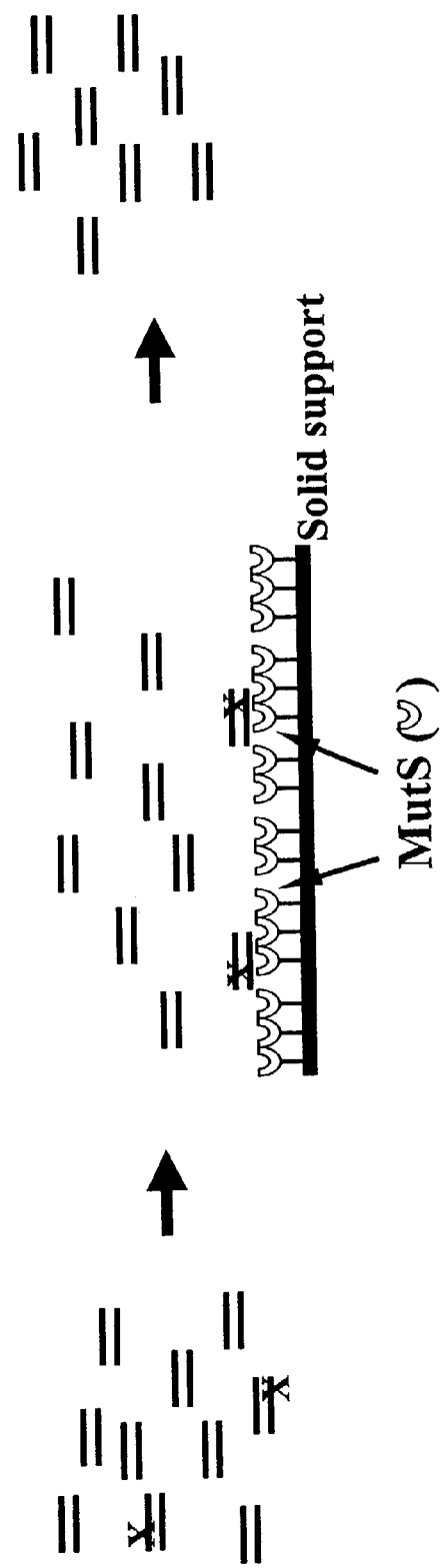
FIG. 3 illustrates schematically the concept of removing DNA of incorrect sequence from a pool of DNA sequences.

FIG. 3 illustrates general concept of "filtering" a pool of DNA strands to remove the errors using the DNA binding agent, such as MutS. An affinity column is prepared with bound MutS available to bind to the DNA strands. The pool of duplex DNA strands are exposed to the affinity column, and those strand which have an irregularity in their helical conformation will bind to the column. The DNA duplexes which are correct in sequence will have no irregularity, do not bind to MutS, and thus pass through the column without binding. Note that there are other methods to select out complexes formed by the binding of the DNA binding agent to the improperly formed DNA duplex. For example, duplex DNA with a binding agent attached migrates through a gel or viscous fluid slower than DNA without the binding agent attached. This permits electrophoresis or liquid chromatography to be used to separate out the DNA with the binding agent attached from the rest of the DNA in a pool.

The main requirements for the DNA binding agent for use in this process is that it binds preferentially to double stranded DNA having a sequence mismatch between its two strands. The preferred agent is MutS, a bacterial protein. MutS from *Thermus aquaticus* can be purchase commercially from the Epicenter Corporation, Madison, Wis., Catalog No. SP72100 and SP72250. The gene sequence for the protein is also known and published in Biswas and Hsieh, *Jour. Biol. Chem.* 271:5040-5048 (1996) and is available in GenBank, accession number U33117. It is therefore readily possible for those of skill in the art to use conventional gene expression vectors transformed into bacteria in culture to produce this protein as well. Another molecule which might be used as the DNA binding agent in this process is CEL1 endonuclease from celery which has a high specificity for insertions, deletions and base substitution mismatches and can detect two polymorphisms which are five nucleotides apart form each other. It is also possible to design and synthesize small organic molecules which will bind to specific nucleotide mismatches, such as dimeric napthyridine 1, a synthetic ligand that binds to a G-G mismatch. A cocktail of such ligands which, in combination, recognize all possible mismatches could replace MutS. Other protein agents that can differentiate between matched and unmatched duplexes could also be used. For example, the T7 endonuclease I will specifically cleave a DNA strand at a mismatch, and it would be possible to use this enzyme as a catalytic destroyer of mismatched sequences or to inactivate the cleavage function of this enzyme for use in this process as a mismatch binding agent. T4 endonuclease VII will specifically bind and cleave DNA at duplex mismatches and a mutant version of this enzyme has already been engineered that lacks the nuclease activity but retains the ability to bind mutant duplex DNA molecules. Golz and Kemper, *Nucleic Acids Research*, 27:e7 (1999). SP nuclease is a highly active nuclease from spinach that incises all mismatches except those containing a guanine residue, and this enzyme could also be engineered to remove the cleavage activity or used directly. Two or more of these binding agents could be combined to either provide further stringency to the filtration or to cover all types of sequence errors if one agent does not bind to all possible mismatches.

It is understood that the invention is not confined to the particular embodiments set forth herein as illustrative, but embraces all such modified forms thereof as come within the scope of the following claims.

EXAMPLES

1. General Protocol for the Synthesis of Double Stranded DNA Sequences (Prophetic)

The synthesis of protected diamine linker and photolabile nucleotide succinates is described in detail in WO 02/095073 which has been incorporated by reference and hence need not be discussed further here.

Preparation of Slides and Oligonucleotide Synthesis (Base Labile Linker)

Microscope slides are prepared as described by Singh-Gasson et. al, Nature Biotechnology 17, 974-978 (1999) yielding a glass surface derivatized with a linker bearing a free alcohol at the terminus. This slide is soaked in an 0.6 M solution of carbonyldiimidazole in dry dichloromethane (6 hours), washed with dry dichloromethane, followed by soaking in a solution MeNPOC-protected diamine (0.4 M) for 12 hours. The slide is then washed with dichloromethane to yield surfaces with secondary amines capped by the photolabile protecting group MeNPOC. In the first 4 cycles of synthesis, the maskless array synthesizer will photo-deprotect the secondary amines in the appropriate array elements for attachment of each of the protected nucleotide-3'-succinates with the coupling reagent O-Benzotriazole-N,N,N'N'-tetramethyluronium-hexafluoro-phosphate (HBTU) in DMF. Unreacted free amines are subsequently capped with acetic anhydride in pyridine. Once the 3'-nucleotides have been attached to the surface subsequent deprotection and elongation cycles are conducted as described in Singh-Gasson et. al. Nature Biotechnology, 17, 974-978 (1999) and as also described in. Published PCT patent application WO99/42813.

Gene Synthesis

In this example, the maskless array synthesizer is used to conduct the synthesis of oligonucleotide fragments on a glass slide. Following release of the oligonucleotide fragments from the slide, the fragments will be assembled into a long double stranded DNA of defined sequence by self assembly and the polymerase chain reaction (PCR), ligase chain reaction (LCR) or both.

For the purpose of this example we consider the synthesis of a double stranded DNA fragment of 420 base pairs in length, of an arbitrary but defined sequence. The target sequence is divided into 20 overlapping 40-mer oligonucleotides. Of the 20 oligonucleotides or segments, 10 are designated for each strand of the target sequence, and the segments are designed to that that they can self assemble into the full length sequence by virtue of the 3'-overhangs of 20 bases on either strand. Software is used to select virtual oligonucleotides from the target sequence and to divide the available array element on the chip evenly for the synthesis of the 20 oligonucleotide fragments. After the synthesis is completed as described above, the slide is incubated with a minimal volume of concentrated ammonium hydroxide and heated to 55° C. for 4 hours, to cleave the oligonucleotides from the surface of the slide and to remove all protecting groups from the bases. The solution is concentrated to dryness in a Speedvac, redissolved in 50 uL of T4 polynucleotide kinase buffer (Promega) and the 5'-hydroxyls of the oligonucleotides are phosphorylated with 20 U of T4-polynucleotide kinase (Promega) at 37° C. for 2 hours. The resulting mixture of phosphorylated oligonucleotides is separated by size on an 8% denaturing polyacrylamide gel electrophoresis. The band corresponding to the full length 40 mer oligonucleotides is excised from the gel and the mixture of oligonucleotides is purified from the gel by freeze/thaw and elution (detailed protocols for each of these procedures can be found in Short Protocols in Molecular Biology 4th edition F. M. Ausubel et. al. Eds. 1999). The purified oligonucleotides are dissolved in LCR buffer (Stratagene) containing 8 U of Pfu DNA ligase (Stratagene). The result of that process is that the individual oligonucleotides are annealed and ligated together to produce a full length DNA sequence by thermal cycling (94° C.-1 min; 40 cycles of: 55° C. for 90 sec, 70° C. for 90 sec, 95° C. for 30 sec; 55° C. for 2 min, 72° C. for 2 min). The full-length oligonucleotide is subsequently amplified by PCR using standard protocols from the LCR reaction using 2 20-mer oligonucleotide primers that are complementary to the 3' overhangs in this example.

The above detailed description of a gene synthesis protocol is provided as an example for practicing the invention. There are many possible variations on this protocol using LCR, PCR or both to anneal and amplify the oligonucleotides into a longer double stranded DNA sequence (Kneidinger et al., BioTechniques, 30, 248-249 (2001); Withers-Martinez et al., Protein Eng. 12, 1113-1120 (1999); Casimiro et al., Structure (London), 5, 1407-1412 (1997); Holowachuk et al., PCR Methods Appl. 1995, 4, 299-302 (1995); Prodromou et al., Protein Eng. 5, 827-829 (1992); Engels, Angew. Chem., 101, 733-52 (1989)). The precise details of this protocol can be altered by a practitioner skilled in the art to optimize the efficiency of the process in a variety of obvious ways such as altering the linker chemistry, the length of the oligonucleotides, the codon usage in each oligonucleotide and thus the hybridization properties of the sequences, the number of oligonucleotides used for construction of each segment, the conditions of the LCR and/or PCR assembly reactions etc. The DNA segments need not be all of the same length, but can be of any desired length within the limits of the quality of segments that can be produced by a given instrument with particular chemistry.

2. Use of Coincidence Filtering (Performed)

General Protocol

In one embodiment of the present invention, DNA oligonucleotides from 20 to 200 bases are synthesized by any method. When the sequence of interest is produced, its anti-sense complement strand is also produced. The sense and anti-sense strands are first denatured by heating to 95°

C., then slowly cooled and allowed to anneal. The double-stranded oligonucleotides are then incubated with a protein or proteins that bind or cleaves oligonucleotides containing base mismatches or deletions (e.g., bacterial MutS). The protein retains or alters the error-containing oligonucleotides while the error-free oligonucleotides are free for further use. The double-stranded oligonucleotides may be then further treated with enzymes to eliminate any remaining errors or single strands. As noted above, mismatches may be located and eliminated by other methods.

Oligonucleotides

The oligonucleotide sequence was derived from the green fluorescent protein UV gene contained in the plasmid pGF-Puv (GenBank accession # U62636). This sequence was chosen because of GFP's as usefulness a reporter gene in future bioassays. Non-mutant or wild-type (wt) anti-sense strands were 5' end-labeled with the fluorescent dye Cy5. Mutant anti-sense strands containing either a deletion or C to A substitution at position 20 were 5' end-labeled with fluorescein. Oligonucleotides were obtained from Operon Inc., Alameda, Calif.

GFPuv 351-390 MP 81.7° C.
Sense    GTTAATGGGCACAAATTTTCTGTCAGTG-GAGAGGGTGAAG (SEQ ID NO:1)
Anti-sense    CTTCACCCTCTCCACTGACA-GAAAATTTGTGCCCATTAAC (SEQ ID NO: 2)
Anti-del 20    CTTCACCCTCTCCACTGAC-GAAAATTTGTGCCCATTAAC (SEQ ID NO: 3)
Anti C>A    CTTCACCCTCTCCACTGAAA-GAAAATTTGTGCCCATTAAC (SEQ ID NO: 4)

Annealing

Figure 5:
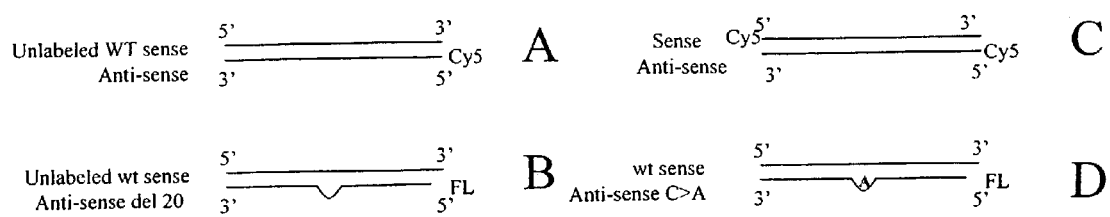
FIG. 5 illustrates the duplexes assembled from oligonucleotides in one of the examples below.

In a typical reaction 80 pmols of unlabeled sense strand were mixed with 40 pmols of Cy5 labeled anti-sense strand and 40 pmols of fluorescein labeled mutant strand (del20 or C>A) in 1× Muts buffer (10 mM Tris-HCl pH 8.8, 5 mM $MgCl_2$, 0.1% TritonX-100). The mixture was annealed in a thermocycler after being first denatured at 95° C. for 5 minutes. The mixture was then cooled at 0.2° C./sec until temperature reaches 25° C. The duplex DNA thus created is illustrated in FIG. 5.

Binding Reaction 2 or 6 μg of $MutS_t$ protein (Epicenter Technologies, Madison, Wis.) was added to the annealed oligonucleotides. The mixture was then incubated at 37° C. for 30 minutes.

Loading dye (Promega 6×) was added to reactions. The entire reaction was loaded onto 6% TBE-PAGE gel amended to be 5 mM $MgCl_2$. (The running buffer of 1× TBE was amended to be 5 mM $MgCl_2$). The electrophoresis was run at 120 volts for 3 hours. Analysis was done on a Molecular Dynamics STORM 860 on both blue (Fluorescein) and red (Cy5) lasers. Molecular Dynamics ImageQuant software was used to quantitate the results.

Results

The wild-type (wt) sense strand was annealed with a 50/50 mix of Cy5 labeled wt anti-sense strand and Fluorescein labeled anti-sense strand containing a deletion at the 20 position. The MutS protein forms a shifted DNA protein complex. The MutS protein preferentially binds the fluorescein labeled double-stranded oligonucleotide containing the deletion at the 20 position (del 20). This result was revealed by the much darker MutS/DNA complex band in the Fluorescein channel on the resulting gel. Protease K was added to the lane digesting away the MutS protein and this digestion eliminated the shifted band, proving the shift was due to protein binding.

To prove that DNA binding by MutS is specific for double-stranded oligonucleotides containing an error, we tried to compete the DNA off the MutS protein with a tenfold molar excess of either unlabeled double-stranded wild-type oligonucleotide (wt) or an unlabeled double-stranded oligonucleotide with a deletion at the 20 position (del20). The results revealed that that a tenfold excess does not cause any type of shifted band in the absence of MutS (No MutS), and with 6 μg of MutS protein, a tenfold excess of wt oligonucleotide doesn't compete away the DNA/MutS complex. At the same time, a tenfold excess of the del20 oligonucleotides did compete away the DNA/MutS complex. This indicates that MutS binding is specific for oligonucleotides with errors.

When producing oligonucleotides using an oligonucleotide synthesizer the most common error is a deletion caused by the failure too remove a blocking group or the failure to couple a base. This experiment showed that MutS protein binds oligonucleotides with a deletion mutation (del20) more efficiently than an oligonucleotide with a A to G mismatch in the middle, as indicated by the darker shifted band in the del 20 lanes runon a gel. In this experiment, the DNA complex showed up in both the Cy5 and Fluorescein lanes because the sense strand was also Cy5 labeled.

Conclusions

The production of double-stranded oligonucleotides allows us to detect and eliminate errors using mismatch specific proteins, such as MutS. The binding of MutS is specific for double-stranded oligonucleotides containing errors. Error containing oligonucleotides can be detected even in a vast excess of non-error containing oligonucleotides. The most common type of error (a deletion) is preferentially detected.

An experiment was conducted to verify the ability of MutS to remove mutant oligonucleotide duplexes from a pool of correct sequences. The oligonucleotides were selected again from the green fluorescent protein native sequence, in this case GFPuv bases numbered 649 to 717, a 68mer. A mutant type 68mer was also created with the deletion of base 33, a T. In a first trial, 22.2 μl containing 2.5 nmoles each of sense and antisense of the correct sequence was placed in a reaction with 1×Taq buffer and 1.5 mM $MgCl_2$. The reaction was denatured by heating to 95° C. for 5 minutes followed by annealing by decreasing the temperature 0.1° C. per second until the reaction reached 25° C. A similar reaction was run in parallel with both wild-type and mutant oligonucleotides combined, the mutant oligonucleotides being spiked in at 0.25 nmoles of the total of 0.25 nmoles of antisense DNA. The two reaction mixtures were each split in halves and incubated with or without MutS. This reaction used 11.1 μl duplex DNA solution containing 1.25 nmoles DNA duplex, 2 μl 75 mM $MgCl_2$, 13.9 μl water, and either (a) 3 μl MutS protein (2 μg/μl or 0.067 nmole) or, in substitution, (b) 3 μg water, for a total reaction volume of 30 μl. The solutions were raised to 37° C. for 30 minutes. Then the entire solutions were loaded into 2.5% agarose gels amended to be 5 mM $MgCl_2$, and run with a buffer that is 1×TBE with 5 mM $MgCl_2$. After electrophoresis, the gel was stained with ethidium bromide. The bands on the gel were analyzed and found to be shifted and unshifted. The unshifted bands were cut out of the gel and the DNA was gel purified using a Qiagen gel purification kit. Aliquots of the DNA recovered were cloned into a Topo-TA plasmid, transformed into *E coli* HB101 cells and plated. Minipreps were prepared from the colonies, DNA recovered and that DNA was sequences. The results of the sequencing analysis was that for the reaction in which the MutS was not included, 30% of the clones were the wild-type or correct sequence, while for the reaction in which the MutS was included, 58% of the clones were the wild-type or correct sequence. This represents a 93% increase in the number of correct wild-type clones in the population. The reason why the percentage of mutant clones so high, when only 10% of the input DNA was intentionally mutant may be due to lack of purity of the oligonucleotides as purchased. But the purification effect is still evident in the data.

Assembly of Sequences with Errors

This experiment was performed to perform a functional assay, looking at expression of the green fluorescent protein to asses error filtering and to try assembly smaller probes into larger DNA assemblies with error sequences being present. The concept was to see if the PCR process would select against the remaining mutant duplexes.

The DNA used in this example were phosphorylated oligonucleotides spanning bases 445 to 585 If the GFPuv sequence. The top and bottom (complementary) strands were made from three 40mers and one 20mer. Within the assembled fragment is a unique restriction site for the enzymes NcoI and BsrGI. The protocol used was to assemble 0.47 nmole of each primer in a total volume of 15 µl in a reaction also including 4 µl of 10×Pfu DNA ligase buffer, 2 µl Pfu DNA ligase (4 µ/µl) and 19 µl water to make a total volume of 40 µl. Ligase chain reactions were run with a temperature profile of 1 minute at 95° C., then 40 cycles of 55° C. for 90 seconds, 70° C. for 90 seconds and 95° C. for 30 seconds, followed by 55° C. for 2 minutes and 70° C. for two minutes.

Figure 4:
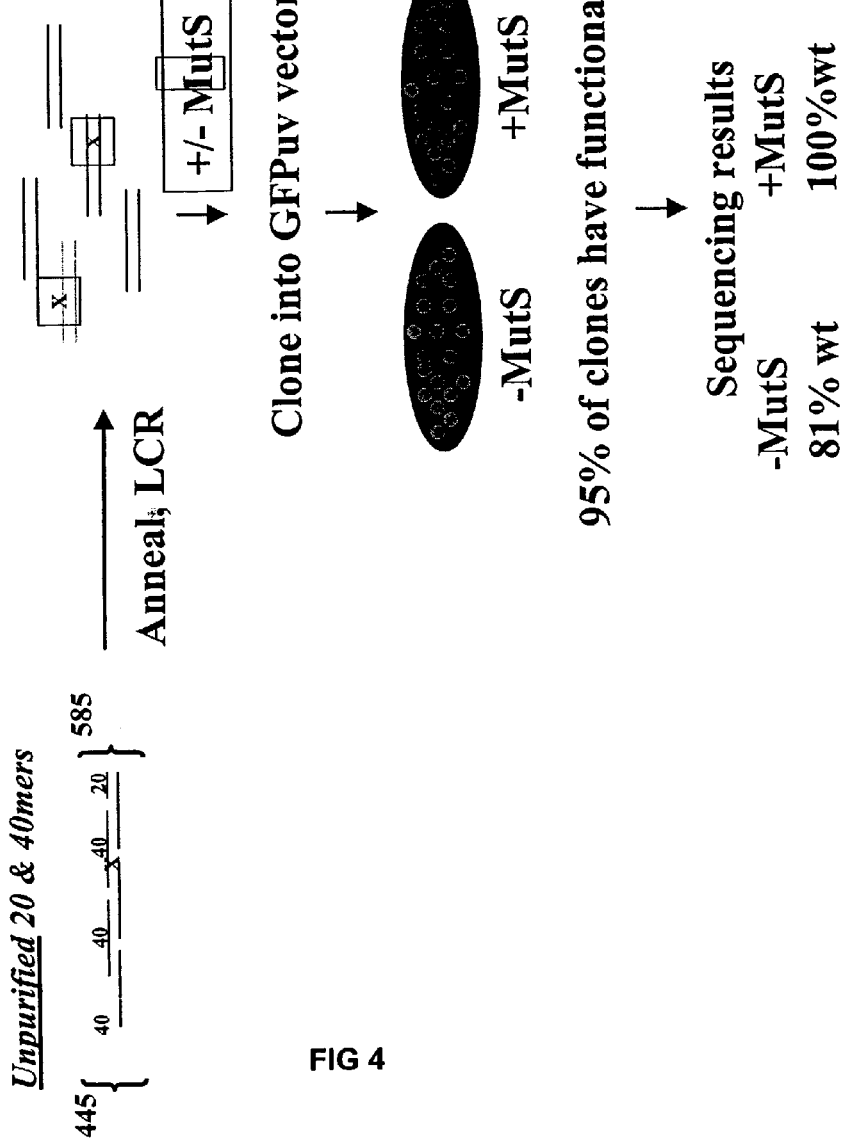
FIG. 4 illustrates the procedure used in the one of the examples below.

To perform the experiments, the reaction mixtures were split into halves, for a total volume of 20 µl, to which was added 5 µl of 75 mM MgCl$_2$, 5 µl of 10×ligase buffer, 22.5 µl MutS protein (2 µg/µl) or 22.5 µl water, and 22.5 µl water for a total volume or 75 µl. The assembled reactions thus each had 0.0235 nmole assembled DNA duplex and 45 µg MutS protein, which acts as a dimer in recognizing and binding to DNA mismatches. The reaction was put at 50° C. for 30 minutes. The total volume was then loaded onto a 2.5% agarose gel amended to be 5 mM MgCl$_2$, with a running buffer of 1×TBE plus 5 mM MgCl$_2$, and run. After electrophoresis, the gel was stained with ethidium bromide and the unshifted bands were cut out of the gel. The DNA was purified using a Qiagen gel purification kit. The DNA was then amplified using the outmost primers. The DNA was digested with Nocd and BsrGI and gel purified. The DNA was ligated into pGVPuv-NcoI-BsrGI and transformed into HB101 cells. This process is illustrated in FIG. 4.

The results of this example were that over 95% of the colonies glowed under UV illumination, after scanning over 750 colonies from both the MutS containing and the MutS negative replicates. Controls with a plasmid not containing GFP did not glow and positive controls with an intact pGFPuv cassette also all glowed. Another negative control using the pGVPuv-NcoI-BsrGI plasmid with no insert also exhibited no glow. This result was somewhat surprising unless (1) multiple deletions or inserts negated the creation of a frameshift or (2) the PCR was biased against amplification of duplexes with mutations. To determine and quantitate the number of possible silent mutations present in the clones, a subset was grown and their DNA was extracted and sequenced. The sequencing reactions revealed that 81% of the colonies from MutS negative pool had the wild-type sequence while 19% harbored the mutant sequence, and all the mutations were substitutions. Of the colonies from the MutS containing reactions, all tested exhibited the wild type or correct sequence. This sequence was confirmed by duplicate sequencing of each colony.

This result demonstrates that a DNA binding agent can successfully be used to separate out minority error sequences from a pool of DNA duplexes created in an LCR reaction. While the GFP functional assay was not diagnostic, the binding of DNA by the MutS was a useful tool in purifying the DNA pool for the desired sequences.

We claim:

1. A method for making DNA sequences of pre-selected defined sequence using a microarray synthesis process that makes occasional errors, the method comprising the steps of
   (a) making a microarray of single stranded DNA probes, the probes constructed so that each probe has a complementary portion that is partially complementary to another probe on the microarray and further constructed so that for each set of probes a complete complementary set of probes is constructed, a minority of the probes in the microarray being erroneously made with a sequence not the defined sequence;
   (b) releasing the single stranded DNA probes from the microarray;
   (c) cooling the single stranded probes so that DNA duplexes are formed, the duplexes formed of probes hybridized to their complete complementary probe having the defined sequence while duplexes formed with single stranded DNA probes not of the defined sequence having an irregularity in its topographical shape;
   (d) exposing the DNA duplexes to a DNA binding agent which will selectively bind to a DNA duplex which has an irregularity in its topographical shape;
   (e) separating out the DNA duplexes to which the DNA binding agent bound;
   (f) denaturing the DNA duplexes to release the single stranded DNA probes from the DNA duplexes;
   (g) cooling the DNA duplexes under conditions which favor at least some of the single stranded DNA probes binding to the probes to which they are only partially complementary to form DNA complexes which are double stranded in at least some part; and
   (h) extending the DNA complexes thus made to add a second DNA strand to remaining single stranded parts of the DNA complexes.

2. A method as claimed in claim 1 wherein the separation is performed by affinity binding the DNA binding agent at a fixed location.

3. A method as claimed in claim 1 wherein the DNA binding agent is MutS.

4. A method for making DNA sequences of pre-selected defined sequence, the method comprising the steps of
   (a) making a microarray of single stranded DNA probes, the probes constructed so that each probe has a complementary portion that is partially complementary to another probe on the microarray, the making of the probes including making a minority of probes which have one or more sequence errors in them, errors being sequences not in the defined sequence;
   (b) releasing the single stranded DNA probes from the microarray;
   (c) cooling the single stranded probes so that a pool of DNA duplexes are formed, the pool of duplexes formed including probes hybridized to their complete complementary probe and having normal topographical shape and other duplexes formed with at least one of the DNA probes in time duplex not of the defined sequence thus creating a duplex having an irregularity in its topographical shape;
   (d) exposing the pool of DNA duplexes to a DNA binding agent which will selectively bind to DNA duplexes which have irregularities in their topographical shapes;
   (e) separating out the DNA duplexes to which the DNA binding agent bound to leave DNA duplexes with the correct defined sequence;
   (f) denaturing the DNA duplexes from the prior step to release the single stranded DNA probes from the DNA duplexes;
   (g) cooling the DNA duplexes from the prior step under conditions which favor at least some of the single stranded DNA probes binding to the probes to which they are only partially complementary to form longer DNA complexes which are double stranded in at least some part; and
   (h) extending the DNA complexes thus made to add a second DNA strand to remaining single stranded parts of the DNA complexes.

5. A method as claimed in claim 4 wherein the separation is performed by affinity binding the DNA binding agent at a fixed location.

6. A method as claimed in claim 5 wherein the DNA binding agent is MutS.

7. A method, as claimed in claim 4 wherein steps (f) through (g) are performed repeatedly to assemble the entire pre-selected DNA sequence desired.

* * * * *